United States Patent [19]

Leynadier et al.

[11] Patent Number: 4,640,897

[45] Date of Patent: Feb. 3, 1987

[54] IMMUNOANALYSIS OF BASOPHIL-CONTAINING BLOOD FRACTION FOR DIAGNOSING PARASITOSES AND ALLERGIES

[75] Inventors: Francisque Leynadier; Hervé Luce, both of Paris, France

[73] Assignee: Institut Pasteur, Paris, France

[21] Appl. No.: 489,603

[22] Filed: May 2, 1983

Related U.S. Application Data

[63] Continuation of Ser. No. 163,736, Jun. 27, 1980, abandoned.

[30] Foreign Application Priority Data

Jun. 28, 1979 [FR] France .................. 79 16772
May 27, 1980 [FR] France .................. 80 11689

[51] Int. Cl.$^4$ .............. G01N 33/566; G01N 33/531; G01N 33/554; G01N 31/00
[52] U.S. Cl. ............................ 436/501; 424/3; 424/7.1; 436/18; 436/513; 436/519; 436/543; 436/807; 436/808; 436/809; 436/811
[58] Field of Search .............. 424/3, 7, 85, 86, 7.1, 424/61, 99, 101; 436/501, 513, 519, 536, 543, 544, 805, 807, 808, 809, 811, 18

[56] References Cited

U.S. PATENT DOCUMENTS 3,900,558  8/1975  Kinsolving ................. 424/8
3,988,115 10/1976  Modabber ................. 23/230 B

FOREIGN PATENT DOCUMENTS 1087966 10/1980 Canada .
2315251  1/1977 France .

OTHER PUBLICATIONS

Leynadier, F., et al., Rev. Franc. Allergol., vol. 17, No. 4, 215–216, 1977 (English translation).
Chemical Abstracts, vol. 88, #134624g, 1978.
Johnson, PSEBM, vol. 123, 1966, pp. 886–888.
Seiverd, Hematology for Med. Tech., Lea and Febiger, Phila., 4th Ed., 1976, p. 679.
Anderson, Nat. Cancer Inst. Monograph 21, Jun. 1966, Development of Zonal Centrifuges and Ancillary Sys. for Tissue Fract. and Analysis, pp. 219–239.
Malveaux, Chem. Abs., vol. 89, 1978, Ab. No. 89:105681p.
Benveniste, Chem. Abs., vol. 88, 1978, Ab. No. 88:134624g.
Conroy, J. Immunology, vol. 118, No. 4, Apr., 1977, pp. 1317–1320.
Gentilini, M. et al., "Diagnostic Biologique de l"hydatidose" *Vie Medicale,* 7 Feb. 1973, pp. 706–712.
Weiss, N. et al., "Radioallergosorbent and Indirect Fluorescent Antibody Tests in Immunodiagnosis of Schistosomiasis", *Lancet,* Dec. 9, 1978, 1231–33.
Capron, A. et al., "Le Diagnostic Immunologique de L'Echinococcose Humaine," *Path. Biol.,* vol. 18, pp. 357–365.
Vervloet, D. et al., "Les IgE Specifiques Dans L'Hydatidoese", *J. Allergy Clin. Immunolog.",* 16, No. 2, pp. 73–78.
Leynadier, F. et al., "Une Technique Simple D'Isolement et de Fixation des Polynucleaires Basophiles Humains", *Rev. Franc. d'Allergol,"* 17, (No. 4), pp. 215–218.

*Primary Examiner*—Esther M. Kepplinger
*Assistant Examiner*—Patricia DeSantis
*Attorney, Agent, or Firm*—Browdy and Neimark

[57] ABSTRACT

The reagent is constituted by a suspension of basophil granulocytes bearing specific IgE's, containing from 300 to 1000 basophils per mm$^3$. This suspension is obtained from a blood sample taken from a human or animal patient, by means of a liquid of density 1.079–1.085. It is deposited in the various wells of a diagnosis read-out slide or the like, for diagnosing parasitoses or allergies. The diagnosis method is applied particularly to worm parasitoses which causes an increase in the circulating specific IgE's. The diagnosis may be carried by using ready-for-use kits.

17 Claims, 4 Drawing Figures

Fig. 3

Fig. 2

IMMUNOANALYSIS OF BASOPHIL-CONTAINING BLOOD FRACTION FOR DIAGNOSING PARASITOSES AND ALLERGIES

This application is a continuation of application Ser. No. 163,736, filed June 27, 1980, now abandoned.

BACKGROUND AND GENERAL DESCRIPTION OF THE INVENTION

The present invention relates to a diagnosis reagent for parasitoses and allergies, to a method for the preparation of this reagent, and to a method of diagnosis of parasitoses and of allergies, notably worm parasitoses which causes an increase in the circulating specific immunoglobulins, such as IgE, $IgG_4$ IgM, by means of this reagent.

Protection of man and of domestic animals against parasitic diseases represents one of the great world problems in the field of public health. If the developed countries have resolved a certain number of their parasitological problems, without, however, having entirely eliminated them, parasitoses still constitutes a major obstacle to the economic development of many countries, and in particular of countries in the hot regions of the globe, which are those which must reckon with the greatest human proliferation.

It is essential, in order to undertake an effective fight against the scourge represented by parasitoses, to be able to carry out a positive, reliable and early diagnosis of parasitoses.

If clinical examination, X-ray examination and information drawn from case histories are of great assistance for establishing a diagnosis, it is essentially due to biological methods and notably immunoparasitological methods that investigation techniques have profoundly developed.

It is at present frequent to refer to a parasitic etiology, a febrile manifestation scarcely judged as "hepatic", "urinary", or "allergic".

Numerous serological techniques have been thus proposed: cutaneous tests by intradermoreaction, agglutination tests of latex particles and of sensitized red blood corpuscles, hemoagglutination tests, precipitation, reactions on gelose, immunoelectrophoretic analyses, tests by immunofluorescence, complement fixation reactions, etc. . . . These up till now conventional diagnosis methods have been able to develop recently, since perfectly known and individualized antigen fractions have been available, and since also, the preservation and stabilization of these antigens has been mastered, as well as their standardization. All these methods have their advantages and their drawbacks; none is infallible. It is thus that A. CAPRON and Coll. (Path. Biol. 1970, Vol. 18, pages 357-365) compare the results obtained for immunological diagnosis of human echinococcosis by the four following methods:

(1) immunoelectrophoresis (I. E.),
(2) hemagglutination (H.M.G.),
(3) agglutination reaction on latex (A.L.), and
(4) the complement fixation reaction (C.F.R.).

The over-all results of the immunological diagnosis of hydatidosis obtained by these authors, are summarized in Table I below.

TABLE I

| Method | Number of patients studied | Number of patients positive | Percentage of positivity | Observed significant minimum | Maximum | Average |
| --- | --- | --- | --- | --- | --- | --- |
| I.E. | 350 | 321 | 91.7% | 1 | 18 | 4.8 |
| R.F.C. | 318 | 227 | 71.4% | ½ | 1/256 | 1/20 |
| H.M.G. | 330 | 260 | 78.8% | 1/512 | 1/512000 | 1/30000 |
| A.L. | 279 | 220 | 78.8% | ½ | 1/512 | 1/50 |

This Table establishes the percentages of positivity, as well as the lower and upper limits obtained for the various methods used. It is noted that immunoelectrophoresis has enabled 91.7% of cases to be detected. In all cases where the existence of a hydatidosis has been positively concluded, the latter has been confirmed by the operational route, and it has never been indicated that an immunological diagnosis is unnecessary. On the other hand A. CAPRON and Collab., have noted that a certain number of patients in whom the immunological response was negative, were indeed hydatidosis carriers. The set-back percentage was 15.4% for I.E., 29% for R.F.C., 21.4% for H.M.G. and 24% for A.L. Another immunodiagnosis method proposed, dealt with the radioallergosorption test or RAST. This test is based on the fact that the patients afflicted with parasitosis have abnormally high specific immunoglobulin E (IgE) levels. The method was described in detail by CESKA and Collab. (J. Allergy Clin. Immunol. 1972, 49, 1). Thus D. VERVLOET and Collab. (Rev. franc. Allergol. 1976, 16 (no. 2), pages 73-78) have used this RAST technique in 60 patients having surgically confirmed hydatidosis and have been able to establish 54 times, namely in 90% of the cases, the presence of IgE's specific with respect to soluble antigens of the hydatic cyst. They have also established a good correlation between the specific IgE levels measured by the RAST and the total IgE level. However, on the other hand, they have not found a correlation between the levels of the IgE antibodies and the level of the antibodies measured by the conventional immunoelectrophoresis techniques of complement fixation, immunofluorescence and hemagglutination. These authors, like also, for example Niklaus WEISS and Collab. ("The Lancet", (Dec. 2, 1978) who have used the RAST in patients infected with Schistosoma heamatobium and S. mansoni, or DESSAINT and Collab. (Immunol. 1975, 29, 813) who have measured the specific IgE's in subjects afflicted with hydatidosis and with bilharziosis, conclude that the RAST can be added to the "conventional battery" of immunological tests, without supplanting them, by reason of its insufficient reliability and due to the fact that it is not a quantitative test, but only qualitative. The histamine determination tests more reliable than the RAST should also be mentioned.

In another field, which is that of allergology, the present inventors, based on the work of SHELLEY (notably in NATURE, 1962, 195, p. 1181-1183; BLOOD, 1962, 19, p. 208-216; Trans. Stud. Coll. Physns Philad., 1964, 32, p. 15-19), taken up subsequently by HIRSCH and ZASTROW (J. Allergy Clin.

Immunol. 1972, 50, p. 338-347) and SOIFER and HIRSCH (J. Allergy Clin. Immunol., 1975, 56, p. 127-132) have applied the degranulation test of human basophile granulocytes with a diagnosis accuracy of the order of 94%, using a leucocyte suspension enriched 10 to 20 times in basophilic granulocytes (with respect to the circulating blood), whose cells are fixed on a slide and dyed with toluidine blue (cf. F. LEYNADIER, H. LUCE and J. DRY, Rev. Franc. d'Allergol., 1977, 17 (no. 4), p. 215-218).

Starting from the knowledge of the fact that the production of considerable amounts of circulating specific IgE's is one of the characteristics of the immune response to the majority of worm parasitoses, the present inventors have sought to adapt the method of measuring IgE's by specific antigens by using suspensions enriched in IgE-carrying basophil granulocytes, placed on slides, which they had previously developed in the domain of allergology, to the diagnosis of various worm parasitoses.

Consequently it is an object of the present invention to provide a diagnosis reagent for parasitoses and allergies, and notably for worm parasitoses, which caused an increase in the circulating specific immunoglobulins fixed on the basophils, such as the IgE's in particular, which reagent enables extremely reliable diagnoses to be obtained and is relatively simple in use, whilst the techniques which enable it to be obtained ensure sufficient concentrations of basophils in the reagent for the results obtained in the presence of antigen, in the course of the diagnosis, to be statistically interpretable with full safety.

Accordingly, the present invention provides a diagnosis reagent for parasitoses and allergies, and notably for worm parasitoses, which cause an increase in the circulating specific immunoglobulins and notably in the IgE's, characterized in that it comprises a suspension of specific IgE-carrying basophil granulocytes, obtained from a blood sample taken from a human or animal patient who is being examined for parasitosis or allergy, which suspension contains from 300 to 100 basophils per $mm^3$, by centrifugation to collect a layer containing essentially leucocytes, which is mixed with a buffer non-destructive relative to basophil cells, such as Hepes buffer or Pipes buffer for example, said homogenized mixture being then deposited on a liquid of density 1.079-1.085 whose osmolarity is comprised between 280 and 320 milliosmoles, to give rise, for centrifugation after a suitable period and at a suitable speed, to a ring which is constituted by a suspension enriched in basophils and which overlies the density liquid, which ring is taken off, then washed, preferably by means of the same buffer as above, to be deposited in different wells of a diagnosis read-out slide or dish.

Accordingly, also the present invention provides a method for the preparation of said diagnosis reagent, which comprises subjecting a blood sample taken from a human or animal patient assumed afflicted with a parasitosis or with an allergy, to a centrifugation for a suitable period and at a suitable speed to collect a leucocyte layer and a supernatant plasma rich in platelets; discarding said plasma and mixing the leucocyte layer with a suitable amount of buffer non-destructive with respect to basophil cells such as Hepes CM buffer or Pipes buffer, for example; injecting under said mixture a liquid of density 1.079-1.085, whose osmolarity is comprised between 280 and 320 milliosmoles, advantageously consisting of a mixture of sodium metrizoate and of Ficoll (Trademark registered by SIGMA) or of Percol (Trademark registered by PHARMACIA); centrifuging for a suitable period and at a suitable speed, to obtain a ring containing the basophils and the lymphocytes; and taking off said ring and washing it carefully with the same buffer as above which is discarded so as to preserve only the cellular cull, which, after resuspending, is ready to be deposited in the wells of a diagnosis read-out slide or dish.

According to an advantageous embodiment of the method of preparing the diagnosis reagent according to the present invention, the Hepes buffer non-destructive with respect to the basophil cells, by means of which the leucocyte layer separated by centrifugation is taken up again, has the following composition:

Hepes buffer, molar solution: 25 ml
KCl 10%: 0.932 ml
$CaCl_2$ 10%: 0.550 ml
$MgCl_2$ 10%: 0.510 ml
NaCl 9% (7.6 g): 844.11 ml
$H_2O$ q.s.p.: 1000 ml According to an advantageous embodiment of the method of preparing the diagnosis reagent according to the invention, the Hepes buffer which is non-destructive with respect to basophil cells, by means of which the leucocyte layer separated by centrifugation is taken up again, has a considerably reduced content of Hepes buffer, and a content of NaCl which is increased with respect to the contents of the above-defined buffer in these substances.

According to an advantageous feature of this embodiment, the quantitative composition of said Hepes buffer is preferably the following:

Hepes buffer, molar solution: 4 to 25 ml
KCl 10%: 0.932 ml
$CaCl_2$ 10%: 0.550 ml
$MgCl_2$ 10%: 0.510 ml
NaCl 9%: 850 to 900 ml
Water q.s.p.: 1000 ml
pH: 7.4-7.6

According to yet another embodiment of the method of preparing the diagnosis reagent according to the present invention, the sampling of a blood specimen in a human or animal patient assumed afflicted with a parasitosis or an allergy, is carried out on ethylenediaminetetraacetic acid, in the form of one of its salts, and preferably in the form of its potassium salt ($K_3$ EDTA), after which the total blood thus drawn, which can be preserved in this form for 24 hours, is mixed with an equal volume of a Hepes buffer of suitable composition, containing heparin in the proportion of 5 to 20 units/ml, then there may either be injected beneath this mixture a liquid of density 1.079-1.085 whose osmolarity is comprised between 280 and 320 milliosmoles, consisting in a mixture of sodium metrizoate and of "Ficoll" (Trademark registered by SIGMA), or of "Percol" (Trademark registered by PHARMACIA), or the heparinated blood Hepes buffer mixture may be transferred into a tube filled previously with the above-mentioned liquid of density 1.079-1.085, to separate the basophils, after which it is centrifuged for a suitable period and at a suitable speed, to obtain a ring containing the basophils and the lymphocytes, which is taken off and washed carefully with the above-said heparinated Hepes buffer which is discarded, after centrifugation, to preserve only the cellular culot which, after re-suspending, is ready to be deposited in the wells of a diagnosis read-out slide or dish.

Due to this modification of the method according to the invention, it is possible to treat blood taken the day before, with quite satisfactory results; in addition, the first centrifugation which, in the method of preparing the diagnosis reagent defined in the first place, follows immediately the taking of the blood specimen, is unnecessary, enabling a reduction in the time of the diagnosis test to at least one hour.

According to the present invention, the heparinated Hepes buffer applied, preferably, in this modification of the method of preparing the diagnosis reagent, advantageously has the following composition:
Hepes buffer, molar solution: 4 to 25 ml
KCl 10%: 0.932 ml
$CaCl_2$ 10%: 0.550 ml
$MgCl_2$ 10%: 0.510 ml
NaCl 9%: 850 to 900 ml
Heparin: 10 to 15 units/ml
Water q.s.p.: 1000 ml
pH: 7.4–7.6
or the following composition:
Hepes buffer, molar solution: 4 to 25 ml
10% KCL: 0.932 to 1.2 ml
9% NaCl: 850 to 900 ml
Water q.s.p.: 1000 ml
pH: 7.4–7.6
in the latter case, the calcium and the magnesium in the form of their suitable salts, are placed in suitable amounts on the diagnosis read-out slides or dishes.

It is also an object of the present invention to provide a diagnosis method for parasitoses and allergies, and notably for worm parasitoses, which cause an increase in the circulating specific IgEs, characterized in that: the diagnosis reagent according to the present invention is placed in contact for about 15 minutes at 37° C., with the specific antigen of the parasitosis or of the allergy that it is desired to diagnose, contained at different concentrations in a certain number of wells of a diagnosis read-out slide or dish, whilst the remaining wells of said slide or dish contain the diagnosis reagent alone, to serve as controls; there follows a rapid drying of the slide soprepared; it is followed by the simultaneous rapid fixing and dyeing, of the slide or of the dish thus prepared, by means of a simultaneous, rapid, hydro-alcoholic fixing and dyeing solution, of suitable composition, which contains a metachromatic dye which selectively dyes the cytoplasmic granules of the basophils, with which the slide or dish is put into contact for a short time, of the order of 5 to 15 minutes, for example; the basophil granulocytes are counted with the optical microscope, with a suitable enlargement (250 to 400 for example), respectively in the control wells and in the various wells containing the reagent and various antigen concentrations; and there is established, by comparison of the reduction in the number of basophil granulocytes (BG) in the wells containing the antigen at various concentrations, with respect to the number of BG contained in the control wells, the degranulation index $$DI = \frac{BG \text{ controls} - BG \text{ antigen}}{BG \text{ controls}} \times 100,$$

or percentage of basophils which have apparently disappeared in the presence of the antigen, which, if it is greater than 35%, enables the detection of the presence of the parasitosis or of the allergy sought.

According to an advantageous embodiment of the method of diagnosis according to the present invention, the simultaneous, rapid hydroalcoholic fixing and dyeing solution for the slides, is a solution with an acid pH, less than 2.5, which contains as the metachromatic dye, toluidine blue, associated with aluminum sulfate, a cetylpyridinium halide, glutaraldehyde and formaldehyde, in solution in a mixture of absolute ethanol and methanol and water.

According to an advantageous embodiment of the simultaneous, rapid fixing and dyeing reagent, applied in the method of diagnosis according to the invention, said reagent is constituted by a hydroalcoholic solution with an acid pH, less than 2.5, which has the following composition:
Toluidine blue or similar metachromatic dye: 2.2 g/liter approx.
Aluminum sulfate: 7.5 g/liter approx.
Cetylpyridinium halide: 0.75 g/liter approx.
Glutaraldehyde: 20 g/liter approx.
Formaldehyde: 35 g/liter approx.
Absolute methanol: 300 ml/liter approx.
Absolute ethanol: 300 ml/liter approx.
Water q.s.p.: 1000 ml According to another advantageous embodiment of the simultaneous, rapid fixing and dyeing reagent solutions, according to the present invention, these solutions have the following quantitative composition:
Toluidine blue or similar metachromatic dye: 0.2 to 0.8%
Aluminum sulfate: 3 to 10%
Cetylpyridinium halide: 0.3 to 0.8%
Glutaraldehyde: 1.5 to 2.5%
30% formaldehyde: 270 to 330 ml
Methanol: 270 to 330 ml
Ethanol: 270 to 330 ml
Water q.s.p.: 1000 ml According to yet another embodiment of these simultaneous, rapid fixing and dyeing solutions, the latter have the following qualitative and quantitative composition:
Toluidine blue or similar metachromatic dye: 0.2 to 0.8%
Aluminum sulfate: 3 to 10%
Cetylpyridinium halide: 0.3 to 0.8%
30% formaldehyde: 300 ml ±10%
Methanol: 300 ml ±10%
Ethanol: 300 ml ±10%
Water q.s.p.: 1000 ml According to another embodiment of these simultaneous, rapid fixing and dyeing solutions, the latter have the following qualitative and quantitative composition:
Toluidine blue or similar metachromatic dye: 0.2 to 0.8%
Aluminum sulfate: 3 to 10%
Cetylpyridinium halide: 0.3 to 0.8%
Methanol: 830 to 990 ml
Water q.s.p.: 1000 ml According to another embodiment of the simultaneous, rapid fixing and dyeing solutions, the latter are distinguished by the fact that they are devoid of formaldehyde, of glutaraldehyde and of ethanol, and that they contain as fixing agent propylene-glycol.

According to an advantageous feature of this embodiment, the qualitative and quantitative composition of these solutions is as follows:
Toluidine blue or similar metachromatic dye 0.2 to 0.8%
Aluminum sulfate 3 to 10%
Cetylpyridinium halide 0.3 to 0.8%

Propyleneglycol 250 ml to 600 ml±10%
Methanol 200 ml to 750 ml±10%
Water q.s.p. 1000 ml According to the present invention, the cetylpyridinium halide utilized is cetylpyridinium chloride or bromide.

In another aspect of the present invention it provides a ready-for-use set, or kit, preferably contained in a single case or box, for the performance of the diagnosis test for parasitoses and allergies, according to the present invention, which kit is characterized in that it comprises, in combination: a plurality of slides, dishes or the like each having a certain number of wells of equal diameter whose totality, except the wells which have to constitute controls, contain a pre-determined amount of a specific antigen of a parasitosis or of an allergy to be diagnosed, which antigen is introduced in the dry state, preferably lyophilized, into each of the wells, said pre-determined amounts varying from one column of wells to the following one; a plurality of tubes containing pre-measured amounts of a suitable buffer such as Herpes CM or Pipes buffer; a plurality of adapted containers such as ampoules, tubes, syringes or the like, each containing a liquid of density 1.079–1.085; at least one container containing a simultaneous rapid hydroalcoholic fixing and dyeing solution, of the above slides, dishes or the like, prepared according to the invention, whose pH is less than 2.5 and which contain a metachromatic dye such as preferably toluidine blue, aluminum sulfate, cetylpyridinium halide, glutaraldehyde and formaldehyde, in solution in a mixture of absolute methanol and ethanol and water.

According to an advantageous embodiment of the ready-for-use kit according to the present invention: each of the wells containing a specific antigen of the parasitosis or of the allergy to be diagnosed contains 10 to 20 μl of said antigen in the lyophylized state; each tube containing a pre-measured amount of buffer containing 5 ml of said buffer; each ampoule, tube, syringe or the like, containing the density liquid contains 5 ml of said liquid of density 1.079–1.085; the or each container containing the simultaneous, rapid hydroalcoholic fixing and dyeing reagent for the prepared slides, dishes or similar, includes a solution of pH less than 2.5, having the following composition:
Toluidine blue or similar metachromatic dye: 2.2 g/liter approx.
Aluminum sulfate: 7.5 g/liter approx.
Cetylpyridinium halide: 0.75 g/liter approx.
Glutaraldehyde: 20 g/liter approx.
Formaldehyde: 35 g/liter approx.
Absolute methanol: 300 ml/liter approx.
Absolute ethanol: 300 ml/liter approx.
Water q.s.p.: 1000 ml According to the invention, the slides, dishes or the like for diagnosis readout utilized, are selected notably from among: slides having a plurality of wells of equal diameter, constituted by paraffin rings; slides on which is glued an adhesive tape previously pierced by a plurality of holes of equal diameter which constitute the wells; transparent plastic dishes at the bottom of which is glued an adhesive tape pierced by a plurality of holes as indicated above.

According to an advantageous embodiment of the kit or set ready for use for the performance of the diagnosis test according to the present invention, the Hepes buffer contained in pre-measured amounts in ampoules or suitable tubes comprises from 4 to 25 ml of a molar solution of Hepes buffer, 0.932 ml of 10% KCl, 0.550 ml of 10% $CaCl_2$, 0.510 ml of 10% $MgCl_2$, from 850 to 900 ml of 9% NaCl, in solution in a sufficient amount of water to bring the solution to 1000 ml, and/or the simultaneous, rapid fixing and dyeing solution of the antigen preparations (or controls) borne by the diagnosis readout slides, contained in the corresponding container, has the following composition:
Toluidine blue or similar metachromatic metachromatic dye: 0.2 to 0.8%
Aluminum sulfate: 3 to 10%
Cetylpyridinium halide: 0.3 to 0.3%
Glutaraldehyde: 1.5 to 2.5%
Formaldehyde 30%: 300 ml±10%
Methanol: 300 ml±10%
Ethanol: 300 ml±10%
Water q.s.p.: 1000 ml
or the following composition:
Toluidine blue or similar metachromatic dye: 0.2 to 0.8%
Aluminum sulfate: 3 to 10%
Cetylpyridinium halide: 0.3 to 0.8%
30% Formaldehyde: 300 ml±10%
Methanol: 300 ml±10%
Ethanol: 300 ml±10%
Water q.s.p.: 1000 ml
or indeed the following composition:
Toluidine blue or similar metachromatic dye: 0.2 to 0.8%
Aluminum sulfate: 3 to 10%
Cetylpyridinium halide: 1.3 to 1.8%
Methanol: 380 to 990 ml
Water q.s.p.: 1000 ml
or again the following composition:
Toluidine blue or similar metachromatic dye: 0.2 to 0.8%
Aluminum sulfate: 3 to 10%
Cetylpyridinium halide: 0.3 to 0.8%
Propyleneglycol: 250 ml to 600 ml±10%
Methanol: 200 ml to 750 ml±10%
Water q.s.p.: 1000 ml According to an advantageous embodiment of the ready-for-use kit according to the present invention, for the performance of the diagnosis test, the latter is composed of a case which comprises: a plurality of adapted containers such as ampoules or tubes containing premeasured amounts of a suitable Hepes buffer, and notably Hepes buffer as defined above, a plurality of ampoules, of tubes or syringes, each containing premeasured amounts of a liquid of density 1.079–1.085, a plurality of diagnosis read-out slides or dishes each having a certain number of wells, of which the major part, with the exception of the control wells, are designed to receive variable predetermined amounts of an antigen specific to an allergy or parasitosis to diagnosed, and a plurality of ampoules or tubes, including premeasured amounts of simultaneous, rapid fixing and dyeing solution, of the above-defined type of solutions.

According to another advantageous embodiment of the ready-for-use kit according to the present invention, the latter is composed of two separate cases of which one, which is intended for the separation of the basophil cells, comprises: a plurality of adapted containers, such as tubes or ampoules containing premeasured amounts of a suitable buffer, notably of the Hepes buffer such as defined above, a plurality of ampoules or of tubes each containing a premeasured amount of a liquid of density 1.079–1.085; and of which the other case comprises: a plurality of diagnosis read-out slides or dishes each having a certain number of wells, of which the major part with the exception of the control wells, are intended to receive variable predetermined amounts of an antigen specific to an allergy or to a parasitosis to be diagnosed, and a plurality of ampoules or tubes including premeasured amounts of a simultaneous, rapid fixing and dyeing solution, or the type of solution defined above, for the performance of the diagnosis test proper.

According to yet another advantageous embodiment of the ready-for-use kit in one or two cases, according to the present invention, the Hepes buffer contained in premeasured amounts in a plurality of adapted containers, such as tubes or ampoules, has the following composition:
Hepes buffer, molar solution: 4 to 25 ml
KCl to 10%: 0.932 ml
$CaCl_2$ 10%: 0.550 ml
$MgCl_2$ 10%: 0.510 ml
NaCl 9%: 850 to 900 ml
Heparin: 10 to 15 units/ml
Water q.s.p.: 1000 ml
pH: 7.4–7.6

According to another advantageous embodiment of the ready-for-use kit in one or in two cases according to the present invention, the Hepes buffer contained in premeasured amounts in a plurality of adapted containers such as tubes or ampoules, has the following composition:
Hepes buffer, molar solution: 4 to 25 ml
KCl 10%: 0.932 to 1.2 ml
NaCl 9%: 850 to 200 ml
Water q.s.p.: 1000 ml
pH: 7.4–7.6
in which case, the diagnosis read-out slides or dishes include, in each of their wells designed to receive antigen, a predetermined amount of calcium and of magnesium in the form of their salts, and notably of their chlorides.

According to an advantageous feature of this embodiment, the calcium is present in the proportion of about 1 mmole/liter and the magnesium is present in the ratio of about 1 mmole/liter.

Besides the foregoing features, the invention comprises still other features, which will emerge from the description which follows.

The invention is aimed more particularly at novel diagnosis reagents, for parasitoses and allergies, as well as at their method of preparation, according to the foregoing features, and the diagnosis methods utilizing said reagent, as well as the means employed to produce said diagnosis methods.

DESCRIPTION OF PREFERRED EMBODIMENTS

The invention will be better understood by means of the additional description which follows, with reference to the examples of preparing diagnosis reagents according to the present invention, to examples of buffers useful for preparing said reagents, to examples of the simultaneous, rapid fixing and dyeing solutions, useful in the method of diagnosis according to the invention, as well as to a diagnosis test by means of said reagent, the results of this test being illustrated by graphs and by the drawing of diagnosis read-out slides in the accompanying drawings.

It must be well understood however, that these examples and drawings are given purely by way of illustration of the invention and do not constitute in any way a limitation thereof.

I

EXAMPLES OF THE PREPARATION OF A DIAGNOSIS REAGENT OF PARASITOSIS OR OF ALLERGY, ACCORDING TO THE INVENTION

Example 1

(a) 5 to 10 $cm^3$ of the total blood specimen are taken from a patient assumed afflicted with parasitosis or allergy which it is desired to detect, the sampling being carried out preferably fasting on a strictly calculated amount of heparin (10 to 15 units per ml).

(b) If the blood is not treated immediately, it can be placed in the refrigerator at a temperature not exceeding 4° C. and for a period not exceeding 3 to 4 hours.

The total blood taken is centrifuged at 130 g to 150 g for 15 minutes, in order to separate the plasma containing the platelets, from a leucocyte layer, which also contains red blood corpuscles.

(c) The supernatant plasma containing the platelets is than taken up and rejected, up to about 2 to 4 mm of the leucocyte layer, this operation being advantageously carried out by means of a syringe provided with a long needle, with a catheter or with a Pasteur pipette.

On the other hand, the leucocyte layer and about 1 $cm^3$ of sub-adjacent red blood corpuscles are recovered.

(d) In a tube, of $100 \times 20$ for example, in which 5 ml of Hepes CW buffer is placed which has the following composition:
Hepes buffer, molar solution: 25 ml
KCl 10%: 0.932 ml
$CaCl_2$ 10%: 0.550 ml
$MgCl_2$ 10%: 0.510 ml
NaCl 9% (7.6 g): 844.11 ml
$H_2O$ distilled q.s.p.: 1000 ml
which is adjusted with ca. ten drops of N NaOH at pH which 7.4 and 7.6;

and of which it is checked that the osmolarity is between 290 and 300 mOsM; for 25 mmoles of buffer, the leucocyte layer and the $cm^3$ of red blood corpuscles recovered are introduced, and it is mixed with the buffer.

(e) By means of a syringe, preferably provided with a long needle of the lumbar puncture needle type, or of a Pasteur pipette, are injected and precaution into the bottom of the tube of step (d), 5 ml of liquid of the density 1.080 which has the following composition:
Sodium metrizoate: 15 g (one ampoule of 20 ml at 75%—product by NYEGAARD, OSLO)
Ficoll (SIGMA): 12.867 g
$H_2O$ q.s.p.: 165.8 ml
the density is adapted precisely to 1.080;
if metrizoate ampoules of 30 ml at 32.8% are used, the amount of Ficoll necessary for one ampoule is 8.441 g with 108.85 ml $H_2O$ q.s.p.

This injection lifts the sub-adjacent diluted blood.

(f) The precaution is taken of not stirring in order that the two media may not mix, and then there follows a centrifugation of 30 minutes at 400 G at the interface (for example, in a JOUAN centrifuger at 1800 rpm with B star).

(g) At the end of the centrifugation, there is observed from bottom to top, about 1 cm of red blood corpuscles, then the liquid of density 1.080, which is separated from the buffer, which is at the upper part, by a ring which contains the basophils and other white cells.

By means of a syringe provided with a catheter, with a long needle or by means of a Pasteur pipette, the ring is taken up cautiously, namely about 1 to 2 ml of liquid.

This ring is washed once in 3 to 5 volumes of Hepes CM buffer; supernatant liquor is rejected to keep only about 0.5 cm³ of the diluted cellular sediment in the buffer.

The cells are then replaced with stirring in suspension in the buffer and the suspension can then be kept at 4° C., until its use in the following two or three hours.

The cell suspension obtained contains from 5 to 10% of basophils in suspension in 0.5 ml of buffer, that is to say, although the number of basophils contained in 1 μl of circulating blood does not exceed 30 or 40, in the cell suspension obtained according to the method according to the invention, an enrichment of the content of basophils is obtained such that the suspension contains from 300 to 1000 basophils per μl.

(h) On the prepared diagnosis read-out slides (compare FIG. 1 appended in which these slides are denoted by the reference numeral 1), that is to say on which an adhesive tape previously pierced with holes of identical diameter is glued, which constitute the wells 2, 3, 4, 5 (see FIG. 1), there is placed inside each of the wells 3, 4, 5, 20 μl of the abovesaid cell suspension, the cells in suspension being distributed regularly in each well. In a certain number of wells, a quarter of them for example, noted by reference 2, is added to the cell suspension, 10 μl of the above Hepes CM buffer; in the other wells, 3, 4, 5, is added to the cell suspension 10 μl of antigen specific to the parasitosis or allergy which it is desired to diagnose, diluted in a Hepes CM buffer.

It is to be noted that the antigen specific to the parasitosis or the allergy that it is desired to diagnose may advantageously come from a sampling carried out in a patient afflicted with the same parasitosis or allergy, of tumoral liquid or allergen liquid which is preserved, until use, by freezing at an optimal temperature of $-80°$ C.

In the embodiment here described, the specific antigen of a parasitosis to be diagnosed is derived from specimens of the liquid content of a hydatic cyst of the liver, itself taken out during a surgical operation, and preserved at $-80°$ C.

To use said hydrate liquid as antigen, it is defrosted, after which it may possibly, but not necessarilly, be centrifuged at 1000 G for 15 minutes.

Supernatant liquid on one hand, the centrifugation culot on the other hand, may both be used as antigen, either in their pure state, or diluted with a Hepes CM buffer.

(i) The slide prepared in this way is placed in a plastic box, whose moisture content is close to saturation.

This box is placed in the drying oven at 37° C. for 15 minutes, the time necessary and sufficient for the reaction between the cell suspension and the antigen to be able to occur.

(j) The dish is then taken out of the drying oven, and then the slide is dried very rapidly by blowing hot air.

The slide is then fixed and dyed simultaneously by means of the following solution:
Toluidine blue: 2.2 g/liter
Aluminum sulfate: 7.5 g/liter
Cetylpyridinium chloride: 0.75 g/liter
Glutaraldehyde: 20 g/liter
Formaldehyde: 35 g/liter
Methanol absolute: 300 ml/liter
Ethanol absolute: 300 ml/liter
Water q.s.p.: 1000 ml
Measured pH: 2.3
in which the slide is dipped for 15 minutes, at the end of which it is rinsed for 30 seconds in water, 30 seconds in absolute ethanol, and if necessary in xylene.

In the case where small transparent plastic dishes for reading the diagnosis are utilized, a suitable amount of the above fixing dyeing solution is poured directly, into said dishes to effect the simultaneous, rapid fixing and dyeing.

Figures 1A, 1B:
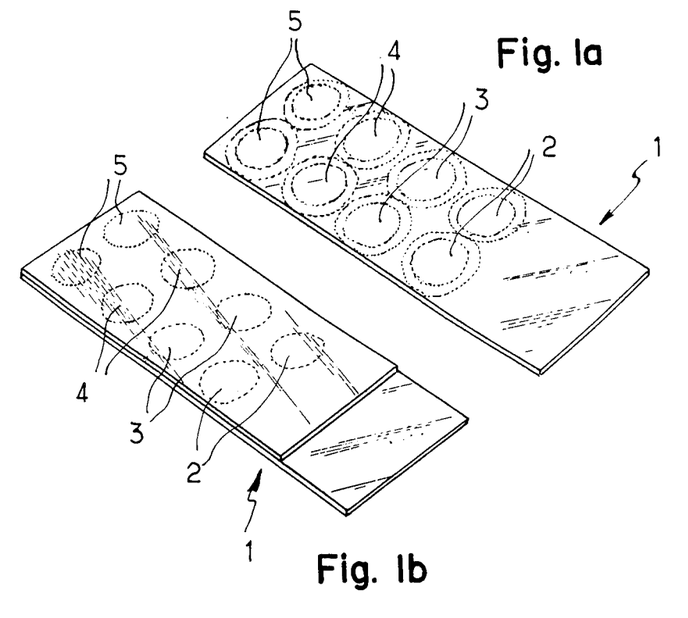

The slide is then mounted by means of a suitable mounting liquid (such as "EUKITT" available from BIOLYON) and a cover slip (cf. slip b in FIG. 1).

(k) The read-out is carried out by counting in the microscope (with an enlargement of 250, 400 or 1000 according to the richness in cells of the suspension) the number of basophils found in the same number of microscopic fields distributed at random in the control wells and in the wells containing the antigen.

The simultaneous fixing and dyeing enable rapid and complete identification of the intact basophils whose number (200 to 1000/μl) and the appearance enable a count close to at least 30 to 50 basophils per control area, which is compatible with statistical analysis.

The degranulation of the basophils which have reacted with the specific antigen, is accompanied by an apparent disappearance of these cells which can then only be identified by their metachromatic effect, in the optical microscope.

The reduction in the number of basophils in the wells containing the antigen with respect to the control wells, is expressed by the degranulation index:

$$DI = \frac{BG \text{ controls} - BG \text{ antigen}}{BG \text{ controls}} \times 100$$

In the presence of a parasitosis or of an allergy, a significant DI is produced, at least greater than 35%, and frequently close to 100%.

Example 2

In a modification, slides are used which are already prepared with the dry antigen inside the wells, such an antigen having been obtained by freeze-drying of the supernatant liquid obtained after centrifugation of the tumoral liquid, as described in Example 1, (h).

Such a preparation of the slides considerably simplifies handling, since it suffices to place 20 μl of cell suspension in all the wells (of which certain, about a quarter, do not contain antigen and serve as controls).

Example 3

The antigen present in the wells of the slide is introduced at various concentrations: for example, in the case of a slide with 8 wells of which 2 wells (the wells 2) do not contain antigen and are hence control wells, the antigen is introduced, into the wells 3 at a dilution of $10^{-4}$, in the wells 4 in a dilution of $10^{-6}$, and into the wells 5 at a dilution of $10^{-8}$, with the Hepes CM buffer mentioned in Example 1.

Example 4

The optical counting described at (k) of Example 1 may be replaced by automatic counting by means of a commercially known machine, such as that which is marketed under the name "OPTOMAX".

It is possible to use, as a variation, simultaneous, rapid fixing and dyeing solutions for the prepared slides, of different compositions than that given in Example 1, (j) above, to improve further the dyeing of said slides.

II

EXAMPLES OF SIMULTANEOUS, RAPID FIXING AND DYEING SOLUTIONS

Example 5

Toluidine blue or similar metachromatic dye: 0.2 to 0.8%
Aluminum sulfate: 3 to 10%
Cetylpyridinium chloride or bromide: 0.3 to 0.8%
Glutaraldehyde: 1.5 to 2.5%
30% formaldehyde: 300 ml±10%
Methanol: 300 ml±10%
Ethanol: 300 ml±10%
Water q.s.p.: 1000 ml

Example 6

Toluidine blue or similar metachromatic dye: 0.2 to 0.8%
Aluminum sulfate: 3 to 10%
Cetylpyridinium chloride or bromide: 0.3 to 0.8%
30% formaldehyde: 300 ml±10%
Methanol: 300 ml±10%
Ethanol: 300 ml±10%
Water q.s.p.: 1000 ml

Example 7

Toluidine blue or similar metachromatic dye: 0.2 to 0.8%
Aluminum sulfate: 3 to 10%
Cetylpyridinium chloride or bromide: 0.3 to 0.8%
Methanol: 900 ml±10%
Water q.s.p.: 1000 ml

Example 8

Toluidine blue or similar metachromatic dye: 0.5%
Cetylpyridinium chloride or bromide: 0.5%
Propyleneglycol: 750 ml±10%
Methanol: 250 ml±10%

Example 9

Toluidine blue or similar metachromatic dye: 0.5%
Cetylpyridinium chloride or bromide: 0.5%
Aluminum sulfate: 5%
Methanol: 750 ml±10%
Propyleneglycol: 250 ml±10%

Example 10

Toluidine blue or similar metachromatic dye: 0.3%
Cetylpyridinium chloride or bromide: 0.5%
Aluminum sulfate: 5%
Propyleneglycol: 400 ml±10%
Water: 200 ml±10%
Methanol: 400 ml±10%

Example 11

Toluidine blue or similar metachromatic dye: 0.5%
Cetylpyridinium chloride or bromide: 0.5%
Aluminum sulfate: 5%
Propyleneglycol: 400 ml±10%
Water: 200 ml±10%
Methanol: 400 ml±10%

Example 12

Toluidine blue or similar metachromatic dye: 0.3%
Cetylpyridinium chloride: 0.5%
Aluminum sulfate: 5%
Prolyleneglycol: 400 ml±10%
Water: 400 ml±10%
Methanol: 200 ml±10%

Example 13

Toluidine blue or similar metachromatic dye: 0.5%
Cetylpyridinium chloride: 0.5%
Aluminum sulfate: 5%
Propyleneglycol: 400 ml±10%
Water: 400 ml±10%
Methanol: 200 ml±10%

The Hepes buffer which is non-destructive with respect to the basophil cells, used to take up the leucocyte layer separated by centrifugation, may have different compositions from that described in Example 1, (d) above.

III

EXAMPLES OF COMPOSITIONS OF HEPES BUFFERS

Example 14

Hépès 1 molar: 10 ml
KCl 10% 0.932 ml
MgCl$_2$ 10%: 0.510 ml
NaCl 9%: 871 ml
CaCl$_2$ 10%: 0.550 ml
Water q.s.p.: 1000 ml
pH: 7.4–7.6

The osmolarity of the buffer is controlled so as to be substantially close (at least within 20%) to that of the plasma.

Example 15

Hepes 1M: 5 ml
KCl 10%: 0.932 ml
MgCl$_2$ 10%: 0.510 ml
NaCl 9%: 880 ml
CaCl$_2$ 10%: 0.550 ml
Water q.s.p.: 1000 ml
pH: 7.4–7.6

The osmolarity of the buffer is controlled so as to be substantially close (within about 20%) to that of plasma.

Example 16

Hepes buffer, molar solution: 4 to 25 ml
KCl$_2$ 10%: 0.934 ml
CaCl$_2$ 10%: 0.550 ml
MgCl$_2$ 10%: 0.510 ml
NaCl 9%: 850 to 900 ml
Heparine: 10 units/ml
Water q.s.p.: 1000 ml
pH: 7.4–7.6

The osmolarity of the buffer is controlled so as to be substantially close (at least within about 20%) to that of plasma.

Example 17

Hepes buffer, molar solution: 4 to 25 ml
KCl 10%: 0.932 to 1.2 ml
NaCl 9%: 850 to 900 ml
Water q.s.p.: 1000 ml
pH: 7.4–7.6

The osmolarity of the buffer is controlled so as to be substantially close (at least within about 20%) to that of plasma.

IV
OTHER EXAMPLE OF PREPARATION OF A DIAGNOSIS REAGENT OF PARASITOSES AND OF ALLERGIES ACCORDING TO THE PRESENT INVENTION

Example 18

(1) a Hepes buffer medium such as described in Example 15 above is reconstituted, that is to say 2 ml of ten times concentrated buffer medium is taken in an ampoule, to which 18 ml of distilled water are added. In this way 20 ml of so-called reconstituted buffer are obtained of which 15 ml are taken up, which are distributed in a centrifugeable tube of 20 ml. To these 5 ml of reconstituted Hepes buffer are added 50 to 250 international units of calcium, lithium, or sodium heparinate. The tube thus prepared is tube (1).

(2) The contents of an ampoule of basophil separation medium (BSM) ready for use, which is the liquid of density 1.079–1.085 mentioned in the present invention, is emptied into a tube of 20 ml with a centrifugeable round bottom. The tube thus prepared is the tube (2).

(3) During fasting 5 ml of veinous blood are taken on $K_3$ EDTA ("Vacutainer" (registered trademark), "Venoject" (registered trademark) or by means of a needle with a tray joined to a tube containing an amount of $K_3$ EDTA such that the final concentration of the $K_3$ EDTA in the blood will be 1.5 mg/ml of blood).

(4) This blood is transferred into the tube (1) which contains the heparinated Hépès buffer (see (1) above) and it is gently homogenized.

(5) The mixture of blood and of homogenized Hép/ès buffer at the surface of the BSM is gently placed in the tube (2) (see 2 above), by means of a Pasteur pipette.

(6) This tube is centrifuged for 30 minutes at 400 G at the interface. At the limit between BSM and the buffer medium is obtained a whitish ring which is taken off completely (1 to 3 ml) by means of a Pasteur pipette mounted on a syringe or pear.

(7) The cellular medium thus obtained, is placed in a centrifugation tube containing the remainder of the heparinated Hepes medium and is washed by a centrifugation of 10 minutes at 150 G. The supernatant liquor is taken off up to the break in slope of the tube (remaining volume ±0.5 ml).

(8) After gentle homogenization for a period of 30–50 seconds by stirring by hand or with the vortex, the cellular clot ready for use is ready for the following step of deposition on the diagnosis read-out slides.

It is to be noted that all the above operations, and notably the centrifugation, are carried out at ambient temperature, about 20° C.

(9) Degranulation reaction

Into each of the wells of a diagnosis read-out slide are placed 20 μl of cell suspension (resuspended clot).

The slide is then placed in a covered dish (Pétri type dish) containing a piece of wet cotton. The whole is placed in the drying oven at 37° C. for 20 minutes.

Then the cover of the dish and the cotton are removed. The slide still in the oven, is then dried in about 15 minutes. The slides may also be dried by a hair-drier.

The fixing/dyeing is obtained by covering each of the wells with a simultaneous rapid dyeing and fixing solution in accordance with one of Examples 5 to 13 above. The slide is left on the support for 15 minutes, then rinsed under a spray of water from the tap (30 seconds), dehydrated in an absolute ethanol bath (30 seconds), and dipped a second into a xylene bath, to facilitate mounting.

A drop of mounting medium is placed on a cover glass. The latter is then applied to the slide. 10 to 15 minutes are necessary to dry the whole (the drying can be accelerated by placing the slide in the drying oven or under a hair-drier).

(10) Reading of the test

It is carried out by the ordinary optical microscope. It is preferable to have "wide-field" objectives and high pieces and of sufficient quality to obtain perfect focussing over the whole of the field.

The enlargement used is variable with the number of basophils. Generally 400, it may be brought to 1000 (immersion) in the case of a great richness of basophils, or on the contrary to 250 if the observer is accustomed.

The basophils are recognized by means of their deep color with respect to the other cells (essentially lymphocytes and monocytes), and especially by the violet color, sometimes red, different from the blue color (light or deep) of the other cells.

The basophils are counted on each of the wells. In the large majority of cases, twenty microscopic fields are sufficient (ten fields at random in a vertical diameter and 10 fields at random in a horizontal diameter). The important thing is, of course, that the same number of fields be examined on each of the wells.

By adding the numbers of basophils found in identical wells A and B, there is obtained:

T = number of basophils without antigen

Ag (1, 2, 3 or 4) = number of basophils with antigen.

The degranulation index (D.I.) is determined for each antigen dilution by the following relationship:

$$D.I. \% = \frac{T - Ag}{T} \times 100$$

V
EXAMPLE OF THE APPLICATION OF THE DIAGNOSIS METHOD ACCORDING TO THE INVENTION

The antigen was obtained from the liquid contents of a hydatic cyst of the liver, taken out during a surgical operation and preserved at −80° C.

After defrosting, the hydatic liquid was centrifuged at 1000 g for 15 minutes. The supernatant liquid on the one hand, and the centrifugation culot on the other hand, were used as pure antigens or diluted with a Hepes CM buffer.

The results were expressed as a percentage of basophils which had apparently disappeared in the presence of the antigen with respect to the number of basophils counted in the presence of the buffer without antigen.

The observation relates to a man aged 38 years, who had a hydatic cyst of 15 cm diameter, developed at the expense of the right lobe of the liver. Its content was translucent with numerous daughter vesicles. The cyst and the hydatic externa were the subject of a complete excision. Immunodiagnosis (electrophoresis and hemagglutination) was negative before the operation; on the fourth day after the operation, the hemagglutination was positive at 1/12,800 and the intradermal injection of decreasing dilutions of liquid sterilized by filtration, showed a positive reaction at 1/100 (15-35), at the 20th minute.

The test according to the invention was done, in the patient, the second and fourth days after the operation and each time in two controls. The four controls were free of any parasitic infestation. One of the controls had a hemolymphangioma of 3420 grams of the right lobe of the liver which was resected.

RESULTS

Figure 2:
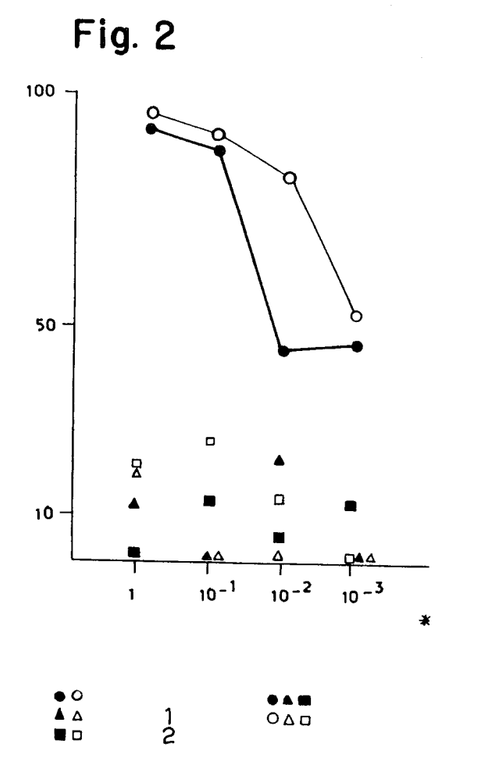
Figure 3:
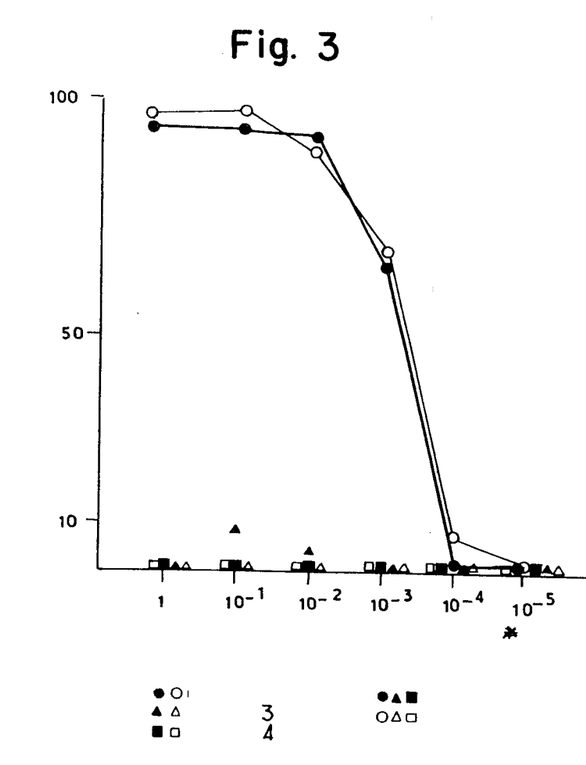

FIGS. 2 and 3 show the percentages of degranulation of the patient and of the two controls on the second day and on the fourth day after the operation. These percentages were established on more than 200 basophils (number actually counted and not extrapolated from some cells counted on the Mallasez slide) for each subject (from 202 to 1270) in the absence of the antigen.

These results show, in this patient afflicted with a hydatic cyst of the liver, a degranulation of the basophils in the presence of hydatic liquid, which is highly significant.

No difference was observed in the results according as the antigen used was hydatic liquid or centrifugation culot.

It results from the foregoing description that there is obtained, according to the invention, means for the realization of a diagnosis test of parasitoses and of allergies involving elevation of specific IgE's which is extremely reliable and gives a concordance percentage with respect to histamine tests, which is close to 100%.

Moreover, the reading of the diagnosis slides is considerably facilitated and accelerated by the increase in the number of basophils to be counted, thus enabling the obtaining of statistically valid degranulation indices.

The diagnosis reagent and the diagnosis test according to the present invention, are applicable to the diagnosis of any parasitoses and allergies which involve an increase in specific IgE's, and notably of helminthiases such as bilharziosis, tenia, ascariosis, filariosis, oxyurosis, etc. . . .

As emerges from the foregoing, the invention is in no way limited to those of its methods of practice, embodiments and uses which have just been more explicitly described; it encompasses on the contrary all modifications which may come to the spirit of the technician skilled in the art, without departing from the scope, nor the spirit, of the present invention.

We claim:

1. A process, for diagnosing parasitoses and allergies which cause an increase of the circulating specific immunoglobins, comprising the steps of:
   selecting a plurality of slides or dishes, each exhibiting a predetermined number of wells of equal diameter all of which, with the exception of the wells that are to act as controls, contain a predetermined amount of an antigen specific to a parasitosis or allergy to be diagnosed, said antigen having been introduced in the dry state in each of the wells, said predetermined amounts varying from one well column to the next,
   a plurality of tubes containing premeasured amounts of a suitable buffer devoid of calcium and magnesium and heparin salts that is not destructive of basophil cells;
   a plurality of suitable containers, each containing a liquid of density 1.079-1.085, and
   at least one container containing a dilute alcoholic solution of a dye, said dye capable of dyeing basophil cells, said alcoholic solution comprising a mixture of ethanol or methanol with water and at least one of glutaraldehyde, formaldehyde or propylene glycol for fast, simultaneous fixing and dyeing of said slides or dishes; wherein said suitable buffer comprises 4-25 ml of Hepes buffer, molar solution, 0.932-1.2 ml 10% KCl, 850-900 ml 9% NaCl and water, q.s. for 1000 ml at pH 7.4-7.6, and wherein each of the wells of said slides or dishes further contain premeasured amounts of calcium and magnesium in the form of their salts,
   mixing a sample of a blood specimen from a human or animal patient assumed afflicted with a parasitosis or with an allergy, with an amount of ethylenediamine tetraacetic acid or one of its sales effective to preserve said blood sample for twenty-four hours;
   mixing the preserved whole blood sample with an equal volume of the buffer devoid of calcium, magnesium and heparin salts from said plurality of tubes containing buffer;
   either injecting under this mixture the density liquid from said plurality of containers containing density liquid or transferring the blood/buffer mixture to one of said containers containing said density liquid;
   removing said ring and washing it with the buffer from said plurality of tubes containing buffer, centrifuging, discarding the buffer supernatant, and resuspending said cellular cull to thereby obtain a diagnostic reagent consisting of a suspension of basophil plynuclears carrying specific IgE'S;
   placing said diagnostic reagent into the wells of said slides or dishes, for about 15 minutes at 37° C.;
   performing simultaneous, fast fixing and dyeing of the prepared slide performed with said fixing and dyeing dilute alcoholic solution from said at least one container to selectively dye the cytoplasmatic granules of the basophils by contacting the slide or dish, for about 5 to 15 minutes, with the solution;
   counting the basophil polynuclears with an optical microscope, respectively in the control wells and in the various wells containing the reagent and various concentrations of antigen; and
   comparing the reduction of the number of basophil polynuclears in the wells containing the antigen in various concentrations with the number of basophil polynuclears contained in the control wells, in order to determine the degranulation index (DI):

$$DI = \frac{\text{control } BP - \text{antigen } BP}{\text{control } BP} \times 100$$

whereby, if the DI is above 35%, the presence of the parasitosis or allergy that is sought may be diagnosed.

2. A process, for diagnosing parasitoses and allergies which cause an increase of the circulating specific immunoglobulins, comprising the steps of:
   selecting a diagnosis kit, including:
   a plurality of slides or dishes, each exhibiting a predetermined number of wells of equal diameter all of which, with the exception of the wells that are to act as controls, contain a predetermined amount of an antigen specific to a parasitosis or allergy to be diagnosed, said antigen having been introduced in the dry state in each of the wells, said predetermined amounts varying from one well column to the next, a plurality of tubes containing premeasured amounts of a suitable buffer that is not destructive of basophil cells;

a plurality of suitable containers, each containing a liquid of density 1.079–1.085, and at least one container containing a dilute alcoholic solution of a dye said dye capable of dyeing basophils, said dilute alcoholic solution comprising a mixture of ethanol or methanol with water and with at least one of glutaraldehyde, formaldehyde or propylene glycol, for fast, simultaneous fixing and dyeing of said slides or dishes;

placing a diagnostic reagent consisting of a suspension of basophil polynuclears carrying specific IgE's into the wells of said slides or dishes containing said antigen for about 15 minutes at 37° C.;

performing simultaneous, fast fixing and dyeing of the prepared slide performed with said fixing and dyeing dilute alcoholic solution to selectively dye the cytoplasmatic granules of the basophils by contacting the slide or dish, for about 5 to 15 minutes, with said solution;

counting the basophil polynuclears with an optical microscope, respectively in the control wells and in the various wells containing the reagent and various concentrations of antigen; and comparing the reduction of the number of basophil polynuclears in the wells containing the antigen in various concentrations with the number of basophil polynuclears contained in the control wells, in order to determine the degranulation index (DI):

$$DI = \frac{\text{control } BP - \text{antigen } BP}{\text{control } BP} \times 100$$

whereby, if the DI is above 35%, the presence of the parasitosis or allergy that is sought may be diagnosed.

3. A diagnostic process in accordance with claim 2, wherein said dilute alcoholic solution for simultaneous, fast fixing and dyeing of the slides or dishes is a solution with an acid pH, less than 2.5, which contains the metachromatic dye, toluidine blue mixed with aluminum sulfate, a cetylpyridinium halide, glutaraldehyde formaldehyde, absolute ethanol, methanol and water.

4. The process of claim 2, further comprising the steps of:

subjecting a blood sample taken from a human or animal patient assumed afflicted with a parasitosis or with an allergy, to a centrifugation for a period and speed sufficient to collect a leucocytic layer and a supernatant plasma;

discarding said plasma and mixing the leucocytic layer with a suitable amount of a buffer which is non-destructive relative to the basophilic cells;

injecting, under said mixture, a liquid of density 1.079–1.088, whose osmolarity is comprised between 280 and 320 milliosmoles;

centrifuging for a period and speed sufficient to obtain a ring containing the basophils and the lymphocytes; and removing said ring and washing it carefully with the same buffer as above, which is rejected in order to preserve only the cellular cull which, after resuspending, is ready to be placed in the well of said diagnosis reading slide or dish.

5. The process of claim 2, further comprising:

mixing a blood sample from the human or animal patient assumed afflicted with a parasitosis or an allergy, with an amount of ethylenediamine tetraacetic acid in the form of one of its salts effective to preserve said blood sample for twenty-four hours;

mixing the preserved whole blood sample with an equal volume of a Hepes buffer of suitable composition, containing heparin in the proportion of 5 to 20 units/ml;

then either injecting under this mixture a liquid of density 1.079–1.085 whose osmolarity is comprised between 280 and 320 milliosmoles or transferring the blood/heparinized Hepes buffer mixture to a tube filled previously with a liquid of the above said density 1.079–1.085, to separate the basophils;

centrifuging for a suitable period and speed, to obtain a ring containing the basophils and the lymphocytes; and removing the samples of said ring and washing with the above said heparinized Hepes buffer, centrifuging and discarding the buffer supernatant after centrifugation, so as only to preserve the cellular cull which after restoring into suspension, is ready to be placed in the well of said diagnosis reading slide or dish containing said antigen therein.

6. A process in accordance with claim 2, further comprising:

mixing a sample of a blood specimen from a human or animal patient assumed afflicted with a parasitosis or with an allergy, with an amount of ethylenediamine tetraacetic acid or one of its salts effective to preserve said blood sample for about 24 hours;

mixing the whole blood thus preserved with an equal volume of a Hepes buffer of suitable composition devoid of calcium and magnesium and heparin salts;

injecting beneath this mixture a liquid of density 1.079–1.085 whose osmolarity is comprised between 280 and 320 milli-osmoles, or transferring the blood-Hepes buffer mixture to a tube filled previously with said liquid of the above said density 1.079–1.085;

centrifuging for a period and speed sufficient to obtain a ring containing the basophils and the lymphocytes; and sampling said ring and washing it with the same Hepes buffer as above which is rejected so as only to preserve the cellular cull which, after resuspending, is ready to be placed in the well of a diagnosis reading slide or box which contains calcium and magnesium in the form of one of their suitable salts as well as said antigen, which are deposited in predetermined amounts.

7. A diagnostic process in accordance with claim 2, wherein said diagnostic reagent is obtained by:

subjecting a blood sample taken from a human or animal patient assumed to be afflicted with said parasitosis or allergy, to a centrifugation for a period and speed sufficient to collect a leucocytic layer and a supernatant plasma;

discarding said plasma and mixing said leucocytic layer with a suitable amount of the buffer from said plurality of tubes containing buffer;

injecting under said mixture the density liquid from said plurality of container containing density liquid;

centrifuging for a time and speed sufficient to obtain a ring containing the basophil and lymphocytes; and removing said ring and washing it carefully with the buffer from said plurality of tubes containing buffer, centrifuging, discarding the buffer supernatant, in order to preserve only the cellular cull which, after resuspending, is used as said diagnostic reagent.

8. A diagnostic process in accordance with claim 2, wherein the buffer contained in said plurality of tubes further includes 5 to 20 units/ml heparin, and wherein said diagnostic reagent is obtained by:
mixing a blood sample from a human or animal patient assumed afflicted with a parasitosis or an allergy, in an amount of ethylenediamine tetraacetic acid in the form of one of its sales effective to preserve said blood sample for twenty-four hours;
mixing the preserved whole blood sample with an equal volume of the heparin-containing buffer from said plurality of tubes containing buffer;
either injecting under this mixture the density liquid from said plurality of containers containing density liquid or transferring the blood/heparinized buffer mixture to one of said containers containing said density liquid;
centrifuging for a period and speed sufficient to obtain a ring containing the basophils and the lymphocytes; and
removing said ring and washing it with the buffer from said plurality of tubes containing buffer, centrifuging, discarding the buffer supernatant, in order to preserve only the cellular cull which, after resuspending, is used as said diagnostic reagent.

9. A kit for making tests of a blood sample to diagnose paraistoses or allergies, comprising:
a case;
disposed within said case, a plurality of suitable containers consisting of ampules or tubes containing predetermined amounts of a suitable Hepes buffer, which is not destructive of basophil cells, exhibiting the following composition:
Hepes buffer, molar solution: 4 to 25 ml
10% KCl: 0.932 ml
10% CaCl$_2$: 0.550 ml
10% MgCl$_2$: 0.510 ml
9% NaCl: 850 to 900 ml
water q.s. for: 1000 ml
pH: 7.4–7.6;
said predetermined amount being an amount effective to form a suspension containing basophils obtained from a blood sample being tested;
disposed within said case, a plurality of ampules, tubes or syringes each containing amounts of a liquid of density 1.079–1.085 effective for isolation of a ring containing basophils from said suspension containing basophils obtained from said blood sample;
disposed within said case, a plurality of slides or dishes for being read to obtain the diagnosis, each exhibiting a predetermined number of wells, which, with the exception of control wells, are adapted to receive variable predetermined amounts of an antigen specific to an allergy or parasitosis to be diagnosed, at least one of said predetermined amounts of said antigen being effective to diagnose said allergy or parasitoses by observation of a degranulation reaction; and
disposed within said case a plurality of ampules or tubes containing an alcoholic dye solution, said dye capable of staining basophil cells, said solution comprising fixing agent, said fixing agent selected from the group consisting of glutahaldehyde, formaldehyde, or propyleneglycol, said fixing agent capable of fixing basophil cells, and dye, in an amount to effect simultaneous fixing and dyeing of said basophil cells.

10. A kit in accordance with claim 9, wherein said case consists of two separate cases of which one, which is adapted for separation of basophil cells, contains said plurality of suitable containers which contain said Hepes buffer and said plurality of ampules, tubes or syringes each containing said amounts of said density liquid and the other of said cases, which is adapted for making the diagnostic test, contains said plurality of slides or dishes and said plurality of ampules or tubes containing said fixing and dyeing solution.

11. A kit in accordance with claim 9, wherein said hepes buffer solution further contains 10–15 units/ml of heparin.

12. A kit for making tests of blood samples to diagnose parasitoses or allergies, consisting essentially of:
a plurality of slides or dishes, each exhibiting a predetermined number of wells of equal diameter all of which, with the exception of the wells that are controls, contain a predetermined amount of an antigen specific to a parasitosis or allergy to be diagnosed, said antigen having been introduced in the dry state in each of the wells, said pre-determined amounts varying from one well column to the next, at least one of said wells having said antigen present in an amount effective to diagnose said parasitosis or allergy by observation of a degranulation reaction;
a plurality of tubes, each tube containing a suitable buffer that is not destructive of basophil cells in an amount effective to form a suspension containing basophils obtained from a blood sample being tested;
at least one container containing a dilute alcoholic solution of a dye, said dye capable of dyeing basophil cells, said solution comprising a mixture of methanol or ethanol, water, and at least one of glutaraldehyde, formaldehyde, or propyleneglycol, in amounts effective for fast, simultaneous fixing and dyeing of said slides or dishes.

13. A kit in accordance with claim 12, wherein each of the wells which contain an antigen specific to the parasitosis or allergy to be diagnosed, and wherein said antigen has been prepared in the freeze-dried state by freeze-drying 10–20 microliters of said antigen; each said tube contains 5 ml of said buffer; each suitable container contains 5 ml of said liquid of density 1.079–1.085; the container or each container which contains said dilute alcoholic solution for fast, simultaneous fixing and drying of prepared slides or dishes, contains, as said alcoholic solution, a solution with a pH less than 2.5, exhibiting the following composition:
methachromatic dye: approximately 2.2 g/liter
aluminum sulfate: approximately 7.5 g/liter
cetylpyridinium halide: approximately 0.75 g/liter
glutaraldehyde: approximately 20 g/liter
formaldehyde: approximately 35 g/liter
absolute methanol: approximately 300 ml/liter
asbolute ethanol: approximately 300 ml/liter
water q.s. for: 1000 ml.

14. A kit in accordance with claim 12, wherein the buffer that is not destructive of basophils contained in premeasured amounts in suitable tubes is a Hepes CM buffer that comprises from 4 to 25 ml of a molar solution of Hepes buffer, 0.932 ml of 10% KCl, 0.550 ml of 10% $CaCl_2$, 0.510 ml of 10% $MgCl_2$, and 850 to 900 ml of 9% NaCl, in solution in an amount of water sufficient to bring it to 1000 ml.

15. A kit in accordance with claim 14, wherein said hepes buffer solution further contains 10–15 units/ml of heparin.

16. A kit in accordance with claim 12, wherein said suitable buffer, comprises 4–25 ml of Hepes buffer, molar solution, 0.932–1.2 ml 10% KCl, 850–900 ml 9% NaCl and water, q.s. for 1000 ml at pH 7.4–7.6, and wherein each of the wells of said slides or dishes further contain an amount of calcium and magnesium in the form of their salts effective for accurate diagnosis.

17. A kit in accordance with claim 16, wherein the calcium is present on said slides or dishes at a concentration of about 1 mmole/liter, and the magnesium is present at a concentration of about 1 mmole/liter.

* * * * *